United States Patent [19]

Cohen et al.

[11] Patent Number: 5,728,083
[45] Date of Patent: Mar. 17, 1998

[54] MULTILAYERED ABSORBENT STRUCTURES

[75] Inventors: Richmond A. Cohen, Warren, N.J.; James A. Minetola, Newtown, Pa.; John F. Poccia, Union Beach, N.J.

[73] Assignee: McNeil-PPC, Inc., Skillman, N.J.

[21] Appl. No.: 430,023

[22] Filed: Apr. 25, 1995

Related U.S. Application Data

[62] Division of Ser. No. 268,400, Jun. 30, 1994, Pat. No. 5,505,719.

[51] Int. Cl.$^6$ .............. B65C 3/26; B29C 33/00; D01G 27/00
[52] U.S. Cl. .............. 604/368; 156/296; 156/62.4; 156/62.6; 156/62.8; 425/81.1; 425/83.1; 19/302
[58] Field of Search .............. 604/358, 365–366, 604/372, 368, 378, 385.1; 428/137, 284, 286, 288, 298, 304.4, 311.7, 311.9, 315.9, 373; 156/296, 62.4, 62.6, 62.8, 209, 276; 425/81.1, 83.1; 19/302

[56] References Cited

U.S. PATENT DOCUMENTS

| | | |
|---|---|---|
| 1,863,333 | 6/1932 | Heitmeyer . |
| 3,029,817 | 4/1962 | Harwood et al. . |
| 3,046,986 | 7/1962 | Harwood . |
| 3,085,575 | 4/1963 | Woskin . |
| 3,105,491 | 10/1963 | Harwood . |
| 3,124,135 | 3/1964 | Olson . |
| 4,093,765 | 6/1978 | Schmidt . |
| 4,223,677 | 9/1980 | Anderson . |
| 4,333,462 | 6/1982 | Holtman et al. . |
| 4,411,660 | 10/1983 | Dawn et al. .............. 604/378 |
| 4,449,979 | 5/1984 | Holtman . |
| 4,531,945 | 7/1985 | Allison . |
| 4,563,289 | 1/1986 | Thompson . |
| 4,578,070 | 3/1986 | Holtman . |
| 4,596,567 | 6/1986 | Iskra . |
| 4,605,402 | 8/1986 | Iskra . |
| 4,670,011 | 6/1987 | Mesek . |
| 4,699,619 | 10/1987 | Bernardin . |
| 4,699,823 | 10/1987 | Kellenberger et al. . |
| 4,713,068 | 12/1987 | Wang et al. . |
| 4,790,839 | 12/1988 | Ahr . |
| 4,798,603 | 1/1989 | Meyer et al. . |
| 4,834,735 | 5/1989 | Alemany et al. . |
| 4,842,594 | 6/1989 | Ness . |
| 4,880,419 | 11/1989 | Ness . |
| 4,883,707 | 11/1989 | Newkirk . |
| 4,908,026 | 3/1990 | Sukiennik et al. . |
| 4,950,264 | 8/1990 | Osborn, III . |
| 4,960,477 | 10/1990 | Mesek . |
| 4,980,226 | 12/1990 | Hellgren et al. . |
| 4,988,344 | 1/1991 | Reising et al. . |
| 4,988,345 | 1/1991 | Reising . |
| 4,994,037 | 2/1991 | Bernardin . |
| 5,009,650 | 4/1991 | Bernardin . |
| 5,009,653 | 4/1991 | Osborn, III . |
| 5,037,409 | 8/1991 | Chen et al. . |
| 5,043,206 | 8/1991 | Ternstrom . |
| 5,047,023 | 9/1991 | Berg . |
| 5,069,676 | 12/1991 | Ito et al. .............. 604/368 |
| 5,124,197 | 6/1992 | Bernardin et al. . |
| 5,134,007 | 7/1992 | Reising et al. . |
| 5,141,794 | 8/1992 | Arroyo . |
| 5,147,343 | 9/1992 | Kellenberger . |
| 5,147,345 | 9/1992 | Young et al. . |
| 5,175,046 | 12/1992 | Nguyen . |
| 5,176,668 | 1/1993 | Bernardin . |
| 5,188,624 | 2/1993 | Young, Sr. et al. . |
| 5,192,277 | 3/1993 | Chung et al. . |
| 5,192,606 | 3/1993 | Proxmire et al. . |
| 5,217,445 | 6/1993 | Young et al. . |
| 5,236,427 | 8/1993 | Hamajima et al. . |
| 5,300,054 | 4/1994 | Feist et al. . |
| 5,304,161 | 4/1994 | Noel et al. . |
| 5,350,370 | 9/1994 | Jackson et al. . |
| 5,350,625 | 9/1994 | Peterson et al. . |
| 5,364,382 | 11/1994 | Latimer et al. . |
| 5,366,451 | 11/1994 | Levesque . |
| 5,368,918 | 11/1994 | Harada et al. . |
| 5,382,245 | 1/1995 | Thompson et al. . |
| 5,399,175 | 3/1995 | Glaug et al. . |
| 5,401,267 | 3/1995 | Couture-Dorschner et al. .......... 604/358 |
| 5,425,725 | 6/1995 | Tanzer et al. .............. 604/368 |
| 5,445,777 | 8/1995 | Noel et al. .............. 425/81.1 |

FOREIGN PATENT DOCUMENTS

| | | |
|---|---|---|
| 0 210 968 | 2/1987 | European Pat. Off. . |
| 0 339 461 | 11/1989 | European Pat. Off. . |
| 0 359 501 | 3/1990 | European Pat. Off. . |
| 0 518 291 | 12/1992 | European Pat. Off. . |
| 2 150 815 | 7/1985 | United Kingdom . |
| 8001455 | 7/1980 | WIPO .............. 604/368 |
| 92/14430 | 9/1992 | WIPO . |

*Primary Examiner*—Robert A. Clarke

[57] ABSTRACT

A multilayered absorbent structure is disclosed. The absorbent structure has a plurality of absorbent planar regions defined by decreasing pore size with increasing depth into the region. Generally, each planar region has an absorbent layer having relatively large average pore sizes at the top, body facing surface, and relatively small average pore sizes at the bottom, garment facing surface. A subsequent absorbent region has a top body facing surface with an average pore size which is larger than the bottom, garment facing surface of the previous absorbent region. The top surface of each subsequent planar region is in fluid communication with the lower surface of the planar region above.

5 Claims, 5 Drawing Sheets

MULTILAYERED ABSORBENT STRUCTURES

This is a division of application Ser. No. 08/268,400, filed Jun. 30, 1994, now U.S. Pat. No. 5,505,719 which is hereby incorporated by reference.

FIELD OF THE INVENTION

The present invention relates to absorbent structures having multiple layers. These structures may be used in diapers, adult incontinence articles, feminine protection such as sanitary napkins, etc. The present invention is particularly useful in absorbent products which receive "gushes" of fluids, but it is also useful in products which accept a more continuous application of fluids at a lower rate.

BACKGROUND OF THE INVENTION

Early construction of disposable hygiene products consisted simply of a topsheet, a pulp or tissue wadding core, and an impermeable backsheet. Significant developments in more recent years have included the move to incorporating superabsorbent materials in the absorbent core. However, devices having only a topsheet, a pulp and superabsorbent core, and a backsheet are outperformed by structures which include a transfer layer (fluid management layer) between the topsheet and the core. The transfer layer might be a fabric layer, a pulp/fiber composite, or even a foam layer. The transfer layer functions to provide a surge capacity for large voids to prevent overflow leakage, to provide capillary suction to draw liquid from the topsheet into the absorbent core, and to retard or inhibit liquid from coming back up through the topsheet and onto the wearer's skin.

Therefore, the challenge is to design each individual transfer layer and to optimize the placement sequence of multiple transfer layers in the product. The manufacturer of a nonwoven material has limited opportunity to affect the absorbency of the material. However, the manufacturer can control the average pore size of the nonwoven material. The pore size is a characteristic of the material that helps to determine its ability to wick fluid and to rapidly transfer fluid, i.e., the permeability of the material.

Measurable characteristics of absorbent structures include rewet and strike-through. Rewet is also described as "surface wetness". It is the amount of absorbed liquid that is detectable at the surface of an absorbent structure after absorption into the absorbent body. In measuring this characteristic, a structure absorbs a given amount of liquid, a given pressure is applied to the structure, and the amount of liquid detectable at the structure's liquid application surface is measured. An absorbent structure exhibiting "good" rewet characteristics would maintain a relatively dry surface, while a structure exhibiting "poor" rewet characteristics would transfer significant liquid back through to the surface of the structure.

Strike-through is the time measured for a given amount of liquid to pass through the facing of an absorbent structure and into its core. An absorbent structure exhibiting "good" strike-through characteristics would quickly accept and absorb applied liquids, while a structure exhibiting "poor" strike-through characteristics would allow applied liquids to form puddles on its surface.

Practitioners in absorbent structure technology have recognized that a positive density gradient, i.e., decreasing pore size with increasing depth into an absorbent structure, improves the performance of the structure. This allows liquids to be accepted into the structure in a region having large pore sizes. However, to improve rewet characteristics, decreasing pore size lower in the structure draws the fluid further into the structure, away from the wearer's skin. This provides a drier surface. It is recognized that decreasing the pore size of a hydrophilic material increases its capillary suction for aqueous liquids. This concept is explored in Meyer, U.S. Pat. No. 4,798,603; Cadieux, EP-A-0 359 501; and Kellenberger, U.S. Pat. No. 4,688,823.

Meyer teaches that the pore size should decrease in progressing from the topsheet to the transfer layer and to the core. In other words, there should be a negative pore size gradient or a positive density gradient. Such a configuration provides a capillary-pressure gradient between each layer, sucking fluid deeper into the absorbent structure, while preventing or reducing rewet.

Cadieux discloses a multiple layered absorbent structure which incorporates a positive density gradient from its cover sheet, through a transfer layer, and to and including a reservoir layer. The cover sheet is disclosed as a relatively low density, bulky, high loft nonwoven web material. The transfer layer may be composed of fibrous materials, such as wood pulp, polyester, rayon, flexible foam, etc., and the reservoir layer is a highly dense absorbent layer having a fine porosity such as compressed peat moss board.

Kellenberger attempts to achieve a concentration gradient in superabsorbent particles distributed within an absorbent fibrous mass or absorbent core. The superabsorbent may be distributed within the absorbent core in a number of concentration gradients: a positive concentration gradient, similar to Cadieux; a bi-nodal concentration gradient, having maxima proximate the top and bottom surfaces, and a minimum concentration at the center of the layer; and a distribution having minimal amounts of superabsorbent proximate the top and bottom surfaces, and a maximum concentration at the center of the layer. This absorbent core can be enclosed between two creped wadding or tissue sheets and used in an absorbent article further having a top cover sheet and a bottom barrier layer.

Other references have provided for multiple layers of absorbent materials in an absorbent structure. These references include Mesek, U.S. Pat. Nos. 4,670,011 and 4,960,477; Iskra, U.S. Pat. No. 4,605,402; Chen, U.S. Pat. No. 5,037,409; Ness, U.S. Pat. Nos. 4,842,594 and 4,880,419; Dawn, U.S. Pat. Nos. 4,338,371 and 4,411,660; and Allison, U.S. Pat. No. 4,531,945.

The prior art generally represents the advance of the absorbent structure art. However, continued advances in this art are needed. In particular, a new absorbent structure is needed which will quickly absorb body fluids, especially gushes of fluids, and strongly contain the absorbed fluids. Such a structure, if easily and economically manufactured, would be very useful in the manufacture of low cost disposable body fluid absorbent articles.

SUMMARY OF THE INVENTION

The present invention relates to a multilayered absorbent structure which will quickly absorb body fluids, especially gushes of fluids, and strongly contain the absorbed fluids. The absorbent structure has a plurality of absorbent planar regions defined by decreasing pore size with increasing depth into the region. Generally, each planar region has an absorbent layer having relatively large average pore sizes at the top, body facing surface, and relatively small average pore sizes at the bottom, garment facing surface. A subsequent absorbent region has a top body facing surface with an average pore size which is larger than that of the bottom, garment facing surface of the previous absorbent region. The top surface of each subsequent planar region is in fluid communication with the lower surface of the planar region above.

In one embodiment of the present invention, the absorbent structure has two planar regions. Each region has two fibrous layers comprising hydrophilic fibers. Each of the layers has a respective average pore size. In the top planar region, the average pore size of the lower fibrous layer is less than the average pore size of the upper fibrous layer. In the lower planar region, the lower fibrous layer has an average pore size which is less than the average pore size of the upper fibrous layer. In addition, the average pore size of the lower fibrous layer in the top planar region is less than the average pore size of the upper fibrous layer in the lower planar region. In essence, descending through the absorbent structure from the liquid accepting upper surface of the top planar region, the average pore size progresses from relatively larger to relatively smaller to relatively larger to relatively smaller.

In a particularly preferred embodiment, the absorbent structure is corrugated by repeatedly folding short lengths of the structure and securing the folds. This type of structure is generally disclosed in Swieringa, U.S. Pat. No. 4,874,457, herein incorporated by reference. This corrugated absorbent structure can then be placed into an absorbent product having a liquid-permeable cover and a liquid-impermeable shell or barrier layer.

The invention also relates to a method of quickly drawing fluids deep into an absorbent structure and locking them in the absorbent structure. The method includes the steps of (1) applying a liquid to an upper porous fibrous layer of a first planar region, (2) drawing the liquid from the upper layer into a lower layer of the first planar region, (3) allowing the liquid to transfer to an upper porous layer of a second planar region comprising hydrophilic fibers and a superabsorbent material, and (4) drawing at least a portion of the liquid from the upper porous layer of the second planar region into a lower porous layer of the second planar region. Each layer of the absorbent structure has an average pore size. The upper layer of the first planar region has a first average pore size, the lower layer of the first planar region has a second average pore size, the upper layer of the second planar region has a third average pore size, and the lower layer of the second planar region has a fourth average pore size. The second average pore size is less than both the first and third average pore sizes, and the fourth average pore size is less than the third average pore size.

DETAILED DESCRIPTION OF THE PREFERRED EMBODIMENTS

Figure 1:
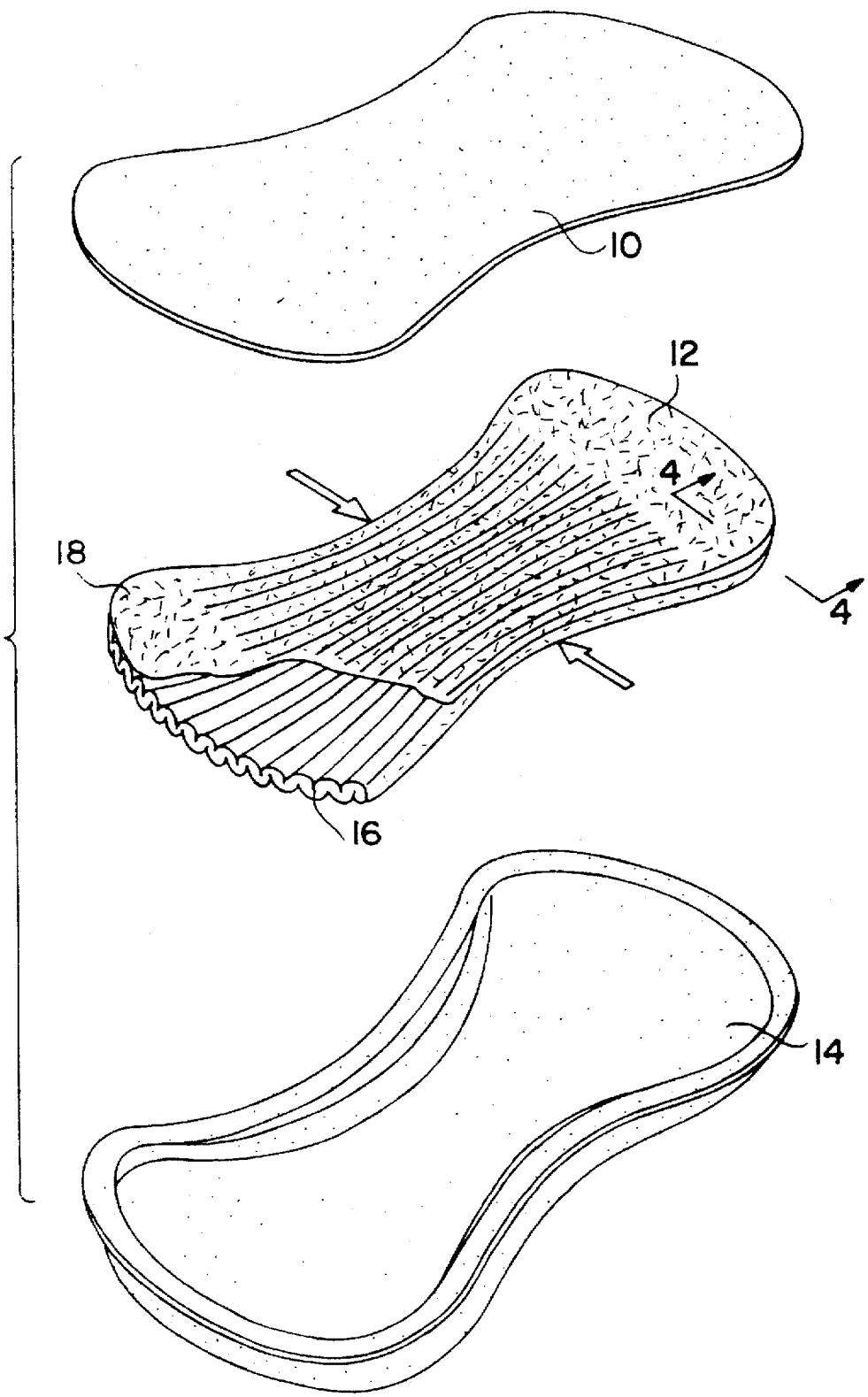
FIG. 1 illustrates an exploded perspective view of an absorbent product having a pleated absorbent core of the present invention.

The present invention relates to a multilayered absorbent structure having a plurality of planar absorbent regions defined by decreasing pore size with increasing depth into the planar region. Generally, each region has an absorbent layer having relatively large average pore sizes at the top, liquid accepting surface, and a fluid management layer having relatively small average pore sizes at the lower surface. There may be additional layers therebetween, each layer having an average pore size no greater than the layer immediately preceding it toward the liquid accepting surface of the planar absorbent region. A subsequent planar absorbent region has a top, liquid accepting surface with an average pore size which is larger than the fluid management layer at the lower surface of the previous absorbent region. Again, this region may include additional layers as described above. Thus, each planar region is defined by generally decreasing average pore size with increasing depth. An increase in average pore size signals the beginning of another planar absorbent region.

It is believed that the use of multiple layers in an absorbent structure having first relatively large then relatively small average pore sizes improves the sequestering of liquids within the absorbent structure. The relatively large pore sizes of the upper, fluid-accepting layers allow these layers to accept gushes of liquid which are then drawn further into the structure by gravity and capillary suction. The second planar region acts to positively draw the liquids accepted by the first, body-facing planar absorbent region further into the structure. The fluid management portion of the second planar absorbent region provides a capillary pressure gradient which assists the upper portion of the second planar absorbent region in drawing fluid from the relatively small pores of the lower layer of the first planar absorbent region.

Pore Size Measurement

There are a number of available techniques useful to measure the average pore size of a nonwoven material. These techniques include the use of the liquid extrusion cell, developed at Textile Research Institute, Princeton, N.J., USA. This technique has been described in Miller et al., "An Extended Range Liquid Extrusion Method for Determining Pore Size Distributions", *Textile Research Journal*, Vol. 56, pp. 35–40 (1986), herein incorporated by reference, and it was used to derive a mathematical model to predict the average pore size of a nonwoven fabric, Cohen, "A Wet Pore-Size Model for Coverstock Fabrics", *Book of Papers: The International Nonwoven Fabrics Conference, INDATEC'90*, Association of the Nonwoven Fabrics Industry, pp. 317–330 (1990), herein incorporated by reference. Based on this model, the following equation was used in the determination of average pore sizes reported in the specification:

$$r = (\Sigma_i x_i \rho_i^2 / \Sigma_i x_i \rho_i)(\rho_f / \xi \rho_w) - 1)/\tau \tag{I}$$

wherein r is the average pore radius;

a is the fiber radius;

x is a number fraction;

$\xi$ is the ratio of dry fabric density to wet fabric density;

$\rho_f$ is the fiber density;

$\rho_w$ is the dry fabric density; and $\tau$ is the tortuosity parameter.

Based upon Cohen's work, the ratio 1.2 was selected for $\xi$, and 1.44 was selected as $\tau$.

The Absorbent Structure

The absorbent structure of the present invention can be used in an absorbent device as illustrated in an exploded view in FIG. 1. In this Figure, there is illustrated a cover sheet 10, an absorbent core 12, and liquid-impervious shell 14. The absorbent core 12 is corrugated to provide a plurality of pleats 16, and the pleats 16 are secured with a facing material 18. The absorbent core 12 may be compressed along its longitudinal edges to fit into the shell 14. The cover sheet 10 may then be secured around the perimeter of the shell 14 to provide the absorbent device.

Figure 2:
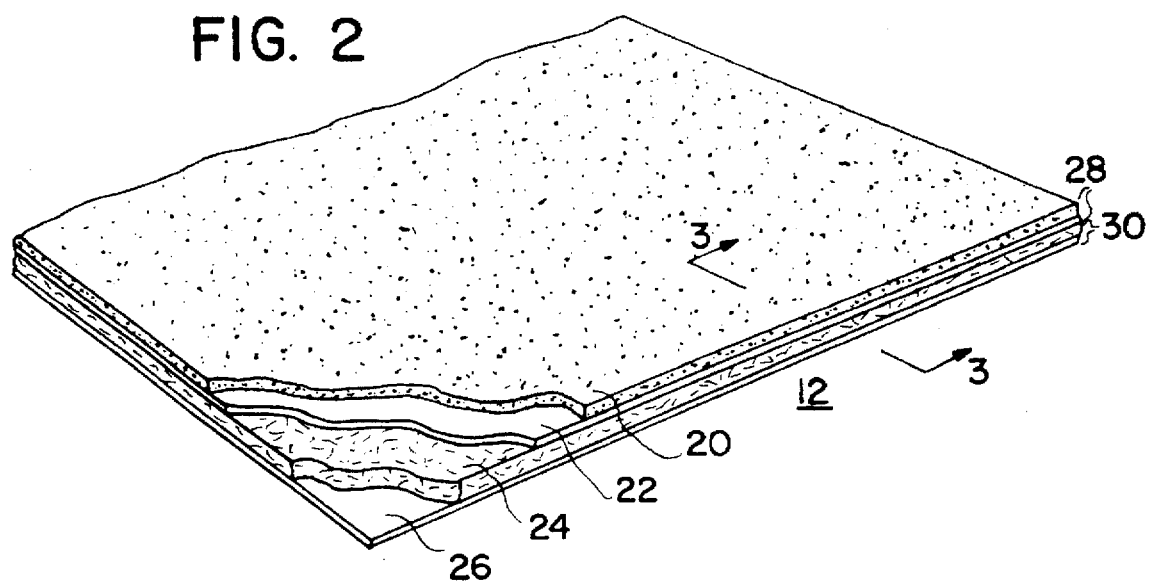
FIG. 2 depicts a partially cut-away perspective view of the absorbent structure in sheet form.
Figure 3:
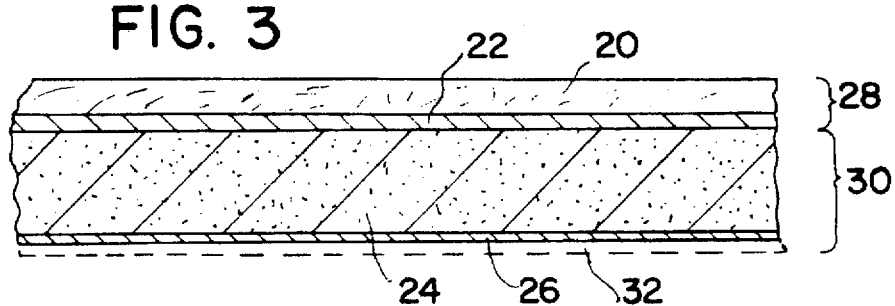
FIG. 3 depicts a cross-sectional view of the absorbent structure of FIG. 2.
Figure 4:
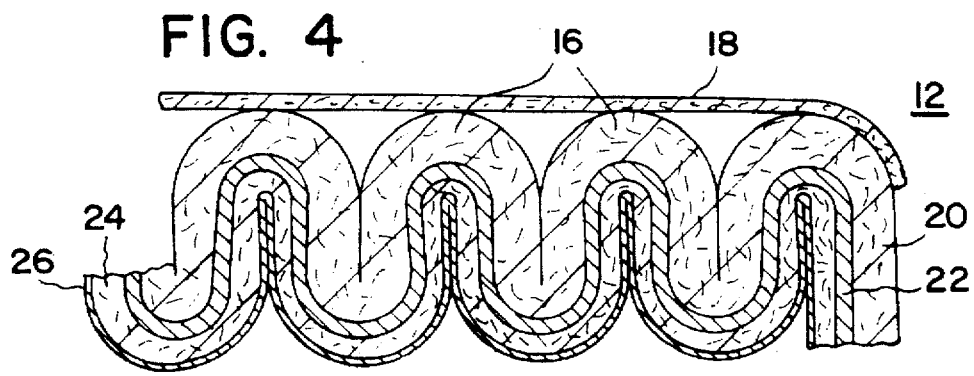
FIG. 4 depicts a cross-sectional view of the absorbent core of FIG. 1.

The pleated absorbent core 12 is illustrated in greater detail in FIG. 4. In this Figure, the facing material 18 can be seen which contacts and is affixed to the pleats 16 along their top ridges. The four layers of the inner structure of the absorbent core 12 can also be seen. The first layer 20 forms the top, liquid accepting layer of the absorbent core 12. The second layer 22 forms the lower layer of the first planar region in this embodiment. The second planar region includes the third layer 24 and the fourth layer 26. This preferred absorbent core 12 is illustrated in a sheet form in FIG. 2. Again, the first and second layers, 20 and 22 form the first planar region 28, and the third and fourth layers 24 and 26 form the second planar region 30. FIG. 3 is a sectional view of the sheet of FIG. 2. This again shows the first planar region 28 formed by the first and second layers 20 and 22 and the second planar region 30 formed by the third and fourth layers 24 and 26. In addition, this Fig. shows an optional fifth layer 32 which may be included as the bottom of the second planar region 30.

Figure 5:
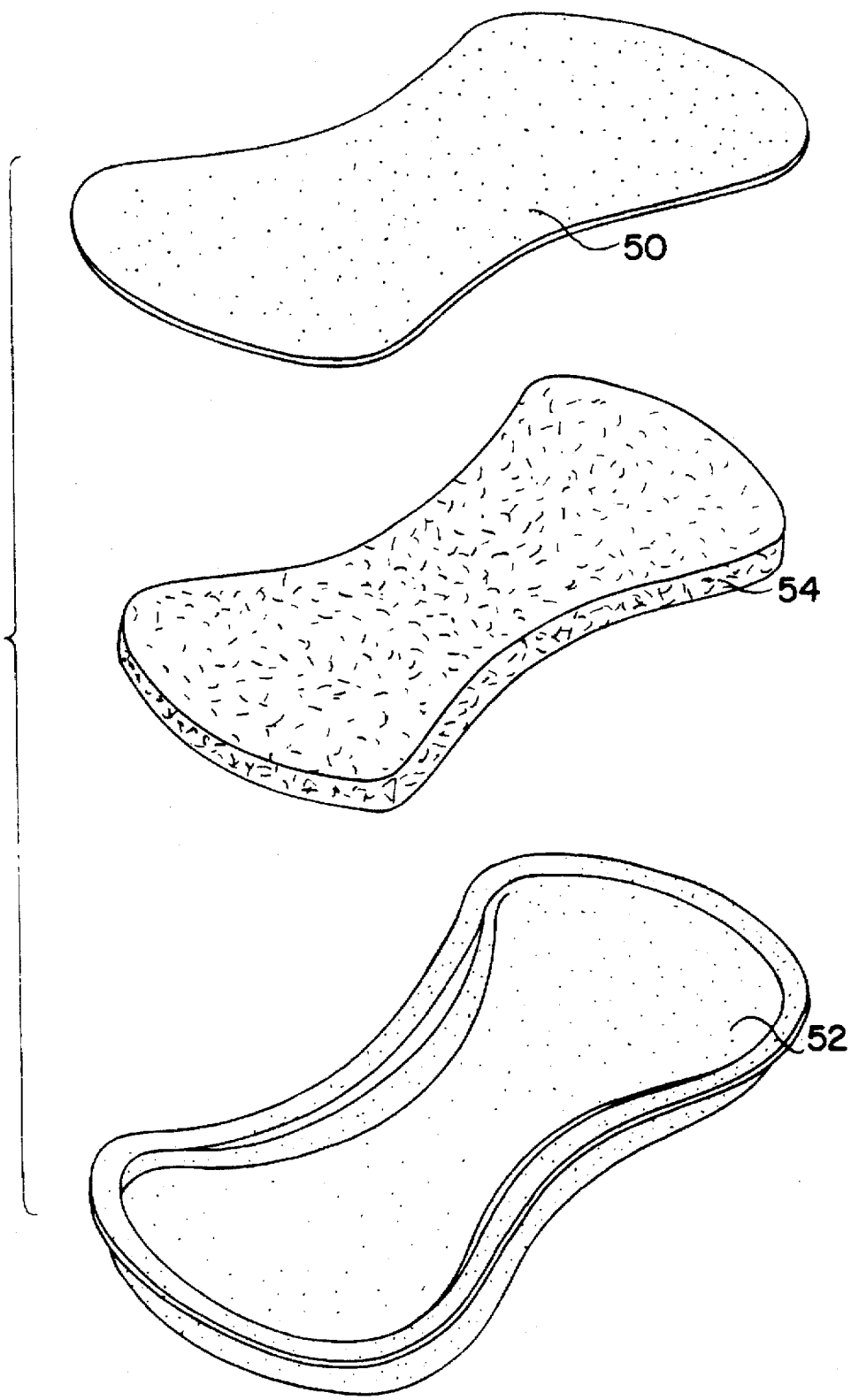
FIG. 5 illustrates an exploded perspective view of an absorbent product having an alternative absorbent core of the present invention.

FIG. 5 illustrates an alternative embodiment of the absorbent product of FIG. 1. In this embodiment, the cover sheet 50 and the liquid-impermeable shell 52 remain essentially unchanged. However, the absorbent core 54 is formed from a flat sheet of absorbent material. For example, the absorbent sheet of FIGS. 2 and 3 may be used, or the absorbent sheet of FIGS. 6 and 7 below, may be used.

Figure 6:
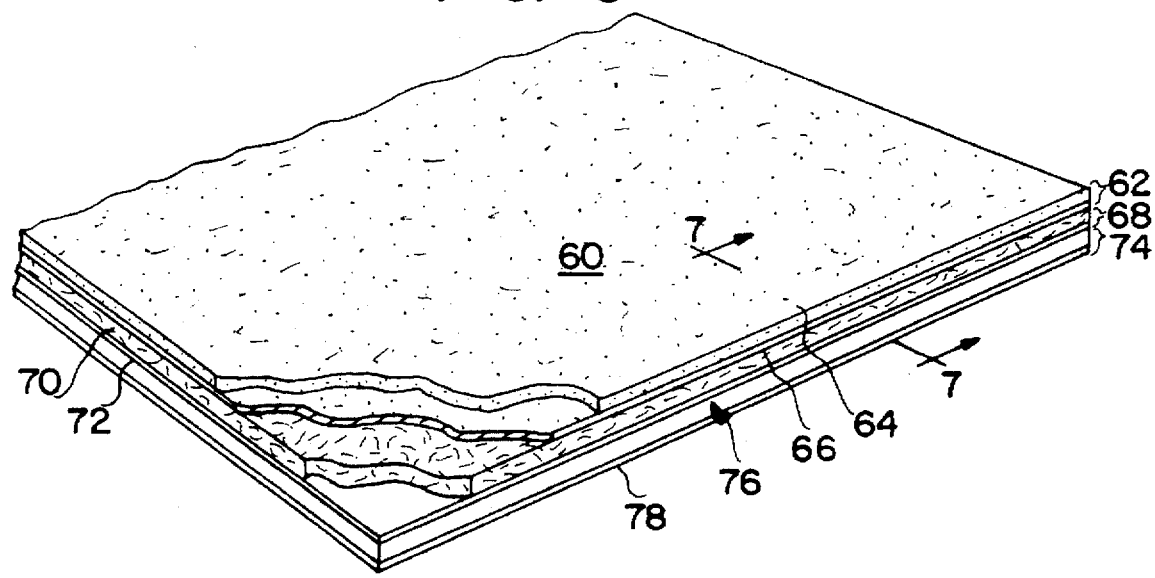
FIG. 6 depicts a partially cut-away perspective view of an absorbent structure having three planar absorbent regions in sheet form.
Figure 7:
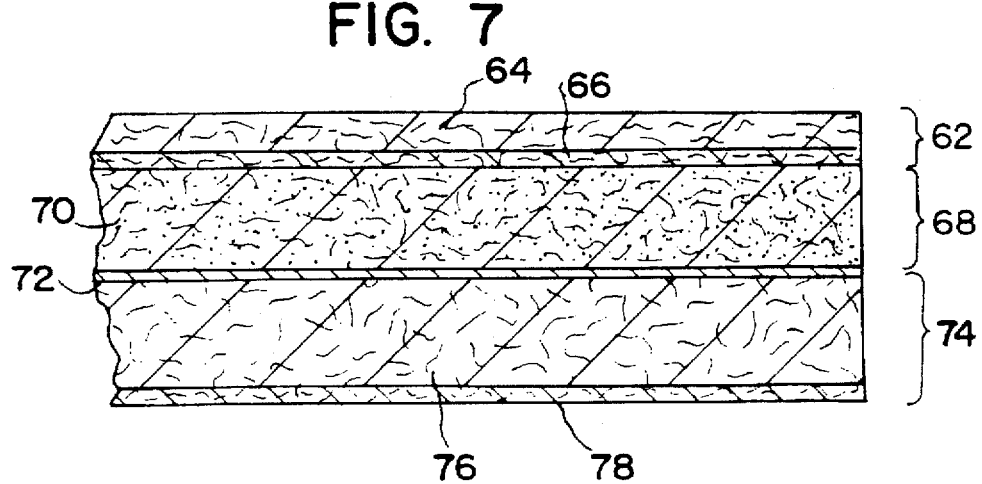
FIG. 7 depicts a cross-sectional view of the absorbent structure of FIG. 6.

FIGS. 6 and 7 illustrate yet another embodiment of the present invention. FIG. 6 illustrates a sheet-like absorbent structure 60 having three planar regions. The first planar region 62 is formed of an upper layer 64 and a lower layer 66. The second planar region 68 is formed of an upper layer 70 and a lower layer 72. The third planar region 74 is again formed of an upper layer 76 and a lower layer 78. FIG. 7 illustrates a sectional view of the structure of FIG. 6.

First Layer

At the body-facing, upper liquid accepting surface, there is a first layer comprising hydrophilic fibers. These fibers may be synthetic or natural fibers or a combination of both. Preferably, the fibers of the first layer are hydrophilic synthetic fibers. These fibers may be formed from hydrophilic polymers, or they may be surfactant-treated hydrophobic fibers. The fibers of the first layer may also be a mixture of hydrophilic and hydrophobic fibers combined in proportion to render the first layer generally hydrophilic.

A representative, nonlimiting list of synthetic fibers which may be used in the present invention includes polyolefin (polyethylene, polypropylene), polyester, rayon, viscose, acrylic, or nylon fibers. In addition, the synthetic fibers can be copolymeric fibers or bicomponent fibers having, e.g., a polyester core and a polyethylene sheath. Bicomponent fibers may be formed from pairs of compatible polymers wherein the inner polymer has higher softening and melting points than the polymer forming the outer sheath. Preferably, the synthetic fibers have a denier of about 1.2 to 15.

A representative, nonlimiting list of natural fibers useful in the present invention includes hemp, jute, cotton, wood pulp, peat moss and the like. These natural fibers may be modified natural fibers, e.g. Weyerhauser HBA and CCF wood pulp fibers, and the like.

The first layer comprises about 10 to 100 wt-% synthetic fibers and 0 to 90 wt-% natural fibers. More preferably, the synthetic fibers comprise the majority of the first layer, and most preferably, the first layer is about 100 wt-% synthetic fibers. The first layer may have an average pore size of about 10 to 1000 μm. In embodiments having both synthetic and natural fibers in any layer, the first layer preferably has an average pore size of about 75 to 400 μm, preferably about 100 to 300 μm, and most preferably about 190 to 250 μm. In embodiments having synthetic fibers in all layers, the first layer preferably has a pore size of about 75 to 1000 μm, preferably about 175 to 600 μm, and most preferably about 185 to 500 μm. The thickness of the first layer can range broadly depending upon the intended use and construction of the absorbent structure. The layer can range from about 0.01 to 0.25 inches in thickness. The layer will generally be thinner if the absorbent structure is to be corrugated or pleated and thicker if the structure is to be used without folding.

Second Layer

Away from the body and in fluid communication with the first layer, there is a second, air-laid layer comprising hydrophilic fibers. These fibers may be synthetic or natural fibers or a combination of both. Preferably, the second layer comprises a mixture of hydrophilic synthetic fibers and natural fibers. The synthetic fibers may be formed from hydrophilic polymers, or they may be surfactant-treated hydrophobic fibers. The fibers of the second layer may also be a mixture of hydrophilic and hydrophobic fibers combined in proportion to render the second layer generally hydrophilic. The synthetic fibers listed above for the first layer may also be used in the second layer. Preferably, the synthetic fibers have a denier of about 1.2 to 15. The natural fibers listed above for the first layer may also be used in the second layer.

The second layer comprises about 10 to 100 wt-% synthetic fibers and 0 to 90 wt-% natural fibers. More preferably, the synthetic fibers comprise the about 40 to 60 wt-% and the natural fibers comprise about 60 to 40 wt-% of the second layer. The second layer may have an average pore size of about 10 to 500 μm. In embodiments having both synthetic and natural fibers in any layer, the second layer preferably has an average pore size of about 40 to 140 μm, preferably about 60 to 120 μm, and most preferably about 80 to 100 μm. In embodiments having synthetic fibers in all layers, the second layer preferably has a pore size of about 10 to 500 μm, preferably about 50 to 180 μm, and most preferably about 100 to 150 μm. The thickness of the second layer can range broadly depending upon the intended use and construction of the absorbent structure. The layer can range from about 0.01 to 0.25 inches in thickness. The layer will generally be thinner, e.g., about 0.01 to 0.03 inches, if the absorbent structure is to be corrugated or pleated and thicker, e.g., about 0.1 to 0.25 inches, if the structure is to be used without folding.

Third Layer

Away from the body and in fluid communication with the second layer, there is a third layer comprising hydrophilic fibers. Again, these fibers may be synthetic or natural fibers or a combination of both. Preferably, the third layer comprises air-laid hydrophilic synthetic fibers. The synthetic fibers may be formed from hydrophilic polymers, or they may be surfactant-treated hydrophobic fibers. The fibers of the third layer may also be a mixture of hydrophilic and hydrophobic fibers combined in proportion to render the third layer generally hydrophilic. The synthetic fibers listed above for the first layer may also be used in the third layer. Preferably, the synthetic fibers have a denier of about 1.2 to 15, more preferably, the fibers have a denier of about 3 to 15. The natural fibers listed above for the second layer may also be used in the third layer.

The third layer preferably also comprises superabsorbent materials. Superabsorbent materials used in sanitary and incontinence products are well known in the art. These materials include polyacrylates; modified natural and regenerated polymers such as polysaccharides; hydrocolloids such as modified polyacrylonitrile compounds; cross-linked nonionic polymers such as polyoxyethylene, polyoxypropylene and mixture thereof; derivatives of isobutylene-maleic anhydride copolymers; copolymers such as those disclosed in U.S. Pat. No. 4,880,868, available from ARCO; and naturally occurring materials such as gums including guar gums, acacia gums, locust bean gums, and the like. The superabsorbent material may be powdered or in fiber form. Preferably, the superabsorbent material is a powdered polyacrylate superabsorbent.

The third layer comprises about 10 to 100 wt-% synthetic fibers, 0 to 90 wt-% natural fibers, and 0 to 80 wt-% superabsorbent material. More preferably, the synthetic fibers comprise about 20 to 60 wt-%, the natural fibers comprise about 20 to 60 wt-%, and the superabsorbent materials comprise about 15 to 60 wt-% of the third layer. The third layer may have an average pore size of about 75 to 1000 μm. In embodiments having both synthetic and natural fibers in any layer, the third layer preferably has an average pore size of about 400 to 1000 μm, preferably about 500 to 900 μm, and most preferably about 600 to 800 μm. In embodiments having synthetic fibers in all layers, the third layer preferably has a pore size of about 75 to 1000 μm, more preferably about 175 to 600 μm, and most preferably about 185 to 500 μm. The thickness of the third layer can range broadly depending upon the intended use and construction of the absorbent structure. The layer can range from about 0.01 to 0.25 inches in thickness. The layer will generally be thinner, e.g., about 0.01 to 0.03 inches, if the absorbent structure is to be corrugated or pleated and thicker, e.g., about 0.1 to 0.25 inches, if the structure is to be used without folding.

Fourth Layer

Away from the body and in fluid communication with the third layer, there is a fourth layer comprising hydrophilic fibers. While this layer may be wet-laid, it is preferably an air-laid layer. The fibers used in this layer may be synthetic or natural fibers or a combination of both. Preferably, the fourth layer comprises a mixture of hydrophilic synthetic fibers and natural fibers. The synthetic fibers may be formed from hydrophilic polymers, or they may be surfactant-treated hydrophobic fibers. The fibers of the fourth layer may also be a mixture of hydrophilic and hydrophobic fibers combined in proportion to render the fourth layer generally hydrophilic. The synthetic fibers listed above for the first layer may also be used in the fourth layer. Preferably, the synthetic fibers have a denier of about 1.2 to 15. The natural fibers listed above for the third layer may also be used in the fourth layer.

The fourth layer may also comprise superabsorbent materials. Useful superabsorbent materials are listed above. Preferably, the superabsorbent material is a powdered polyacrylate superabsorbent.

The fourth layer comprises about 10 to 100 wt-% synthetic fibers, about 0 to 90 wt-% natural fibers and about 0 to 80 wt-% of a superabsorbent +material. More preferably, the synthetic fibers comprise the about 20 to 60 wt-%, the natural fibers comprise about 20 to 60 wt-% and the superabsorbent material comprises about 15 to 60 wt-% of the fourth layer. The fourth layer may have an average pore size of about 10 to 500 μm. In embodiments having both synthetic and natural fibers in any layer, the fourth layer preferably has an average pore size of about 40 to 140 μm, preferably about 60 to 120 μm, and most preferably about 80 to 100 μm. In embodiments having synthetic fibers in all layers, the fourth layer preferably has a pore size of about 10 to 500 μm, preferably about 50 to 180 μm, and most preferably about 100 to 150 μm. The thickness of the fourth layer can range broadly depending upon the intended use and construction of the absorbent structure. The layer can range from about 0.01 to 0.25 inches in thickness. The layer will generally be thinner, e.g., about 0.01 to 0.03 inches, if the absorbent structure is to be corrugated or pleated and thicker, e.g., about 0.1 to 0.25 inches, if the structure is to be used without folding.

Subsequent Layers

While the present invention is described herein with reference to two planar regions comprising four layers in all, in certain applications, it may be helpful or necessary to include additional layers. These layers should generally be included in planar regions to result in the absorbent structure having the following progression of relative pore sizes: large, small, large, small, large, small, etc. Of course, there may be one or more planar regions having the following progression of pore sizes: large, medium, small; large, large, small; large, small, small; and the like. In addition, the subsequent planar absorbent regions may also incorporate superabsorbent materials.

How to Make

The multilayered absorbent structure of the present invention can be formed by laminating or combining individual nonwoven fabric webs, or it can be prepared by forming several different nonwoven fabric layers in a continuous process. Preferably, the absorbent structure is prepared by combining two separate nonwoven structures having several layers to provide the plurality of planar regions having a decreasing pore size gradient within each planar region.

The absorbent webs which make up the planar regions can be prepared by methods known to those of ordinary skill in the art, using conventional grinding equipment such as M&J equipment available from M&J Company of Sweden, Williams mills, Fitzmills, available from Fitzpatrick Co., and a dual rotor webber, available from J.D. Hollingsworth on Wheels, Inc., Greenville, S.C. In addition, synthetic fiber-rich structures can be thermobonded, melt-blown, spunbonded, formed with conventional air-laid equipment, such as card-and-bind equipment, and the like.

In a preferred embodiment, two fabric webs are combined to form an absorbent structure of the present invention having two planar regions of decreasing average pore size.

The first fabric web, which forms the bottom portion of the absorbent structure, may include an optional bottom layer of 0.15 oz/yd$^2$, 1.8 denier synthetic bicomponent fiber (BASF 1051, polyethylene over polyester terephthalate (PET), available from BASF Fibers, Williamsburg, Va.), a second layer of a uniform blend of 0.4 to 0.6 oz/yd$^2$, 3 denier synthetic bicomponent fiber (BASF 1050, polyethylene over PET) and 1 to 1.5 oz/yd$^2$ cellulosic pulp fibers (Rayonier Pulp E-Type, available from Rayonier, Inc., Stamford, Conn.), and an upper layer of a uniform blend of 0.1 oz/yd$^2$, 10 denier synthetic bicomponent fiber (BASF 1088, polyethylene over PET) and 0.1 oz/yd$^2$, 15 denier synthetic PET fiber (duPont 374W, available from E.I. dupont de Nemours, Textile Fibers Department, Wilmington, Del.). The upper layer is carded onto a mesh belt. The synthetic fiber/pulp layer is then formed in a dual rotor webber on the upper layer, and the optional synthetic fiber layer may be carded on the synthetic fiber/pulp layer. The structure is then thermally bonded in an oven.

The second fabric web, which forms the upper portion of the absorbent structure, includes a bottom layer of a uniform blend of 0.1 oz/yd$^2$, 10 denier synthetic bicomponent fiber (BASF 1088) and 0.1 oz/yd$^2$, 15 denier synthetic PET fiber (duPont 374W), a second layer of a uniform blend of 0.4 oz/yd$^2$, 3 denier synthetic bicomponent fiber (BASF 1050) and 0.5 oz/yd$^2$ cellulosic pulp fibers (Rayonier Pulp E-Type), and an upper layer of about 0.4 oz/yd$^2$, 3 denier synthetic bicomponent fiber (BASF 1050). The upper layer is again carded onto a mesh belt. The synthetic fiber/pulp layer is then formed is a dual rotor webber on the upper layer, and the 3 denier bicomponent fiber layer is carded on the synthetic fiber/pulp layer. This structure is also thermally bonded in an oven.

The two webs are then combined in an absorbent structure manufacturing process. The bottom web is first unwound onto a carrier belt. A superabsorbent powder and optional materials including odor control powder or liquid can be deposited onto the top surface of the bottom web. Next, the top web is unwound onto the bottom web. This web may be adhered to the bottom web. The edges, and optionally a random pattern across the web, may then be embossed to increase the integrity of the absorbent structure. The embossing may be performed with or without added heat.

The contact of the two fabric webs forms an absorbent structure having two superposed planar regions. The upper planar region includes, from the top surface, (1) a 3 denier synthetic bicomponent fiber layer and (2) a blended layer of 3 denier synthetic bicomponent fiber and cellulosic pulp. The lower planar region includes, from the upper surface, (1) the merged synthetic bicomponent fiber/synthetic PET fiber web of the first and second fabric webs comprising superabsorbent powder, (2) a blended layer of 3 denier synthetic bicomponent fiber and cellulosic pulp and (3) the optional 1.8 denier synthetic bicomponent fiber layer. The formation of the absorbent structure is completed with the embossing of the structure.

The absorbent structure may then be further processed into an absorbent article. This processing includes corrugating the structure, applying a bicomponent bonding veneer, and heating the corrugated structure with the bonding veneer to thermobond the veneer to the structure to maintain the corrugation. The bonding veneer may be, for example, 0.5 oz/yd$^2$, 3 denier synthetic bicomponent fiber (BASF 1050). After the structure has been bonded, the edges of the structure may be embossed to seal them. This corrugation is taught in Swieringa, U.S. Pat. No. 4,874,457. A masking layer may be adhered to the upper surface of the bonding veneer, and absorbent pads may be slit from the structure. The absorbent pads are then placed into a formed foam shell and covered, for example, with nonwoven web of 0.7 oz/yd$^2$, 3 denier synthetic bicomponent fiber (BASF 1050) facing veneer, and the products are cut from the foam shell material web. While the above method of making relates to a particular process and product, it will readily be recognized that this process can be modified, e.g. by adding additional powders, etc, to the superabsorbent-containing layer, by adding additional planar absorbent regions, and the like. In addition, the products may be manufactured in a single line, or in multiple manufacturing lines. The products may be formed by stamping out the products via conventional cutting methods, e.g., die cutting, flying knives, and the like.

How to Use

Using the method described above or other processes known to those of ordinary skill in the art, the absorbent structure may be incorporated into any suitable absorbent product such as a sanitary napkin, diaper, adult incontinence device, and the like. In one preferred embodiment, the absorbent structure is incorporated into an adult incontinence device described in the commonly assigned application, Poccia et al., U.S. Ser. No. 08/184,402, filed Jan. 20, 1994, now pending, herein incorporated by reference. In such a device, the absorbent structure is preferably corrugated and bonded to a layer of nonwoven fabric to maintain the stability of the structure. The corrugated structure may be combined with additional fluid management layers and masking layers before being enclosed by a cover layer and a fluid impervious backing shell.

Of course, the absorbent structure need not be corrugated or pleated in use in an absorbent product. For example, FIGS. 2, 3, 6 and 7 illustrate a thicker absorbent structure useful in absorbent products.

Test Method Used

The following test method can be used to measure properties of absorbent structures according to the present invention:

PENETRATION TIME AND INCREMENTAL SURFACE WETNESS

The test method measures the penetration time and surface wetness. The penetration time is the time taken for a given amount of liquid to pass through the facing and be absorbed into an absorbent structure. Surface wetness measures the amount of liquid that passes from the standard core material through a cover facing, to cause wetness on the surface of the product.

Figure 9:
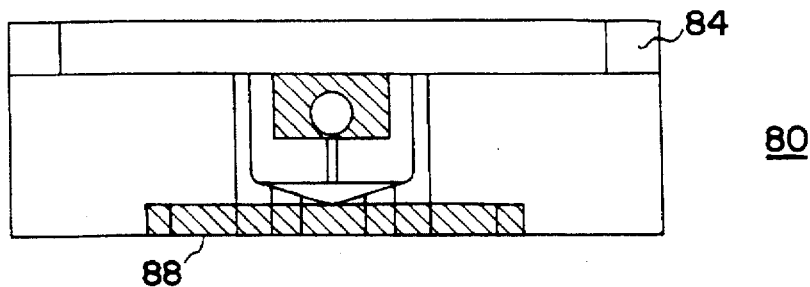
FIG. 9 is a side elevation of the strike-through plate of FIG. 8.
Figure 8:
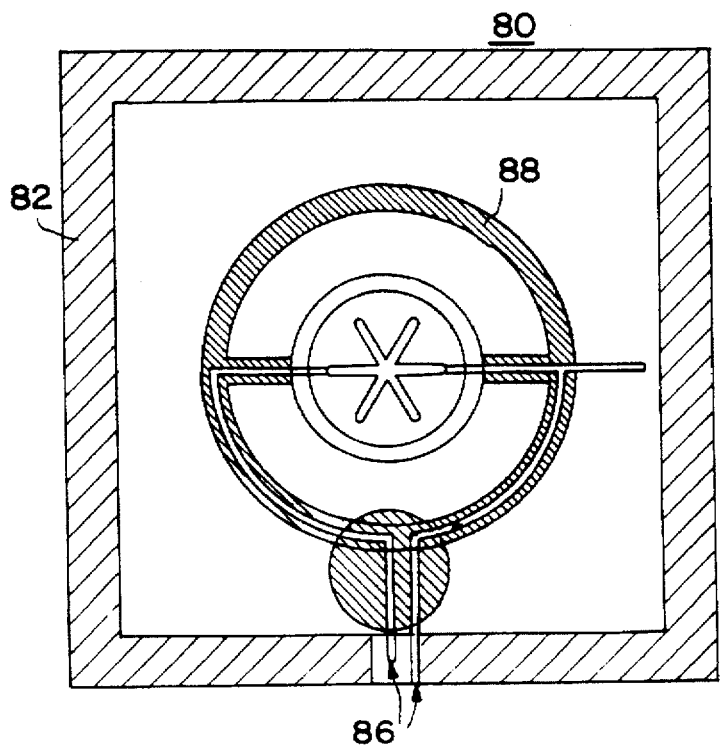
FIG. 8 depicts a plan view of the strike-through plate of the test apparatus.
Figure 10:
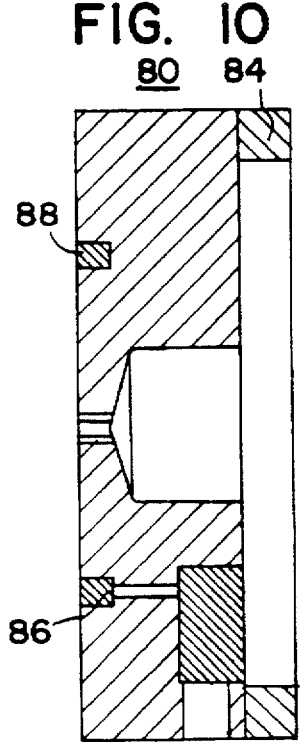
FIG. 10 is a second side elevation of the strike-through plate of FIG. 8.

This test uses the following equipment:
1. Calibrated stopwatch/timer accurate to 0.1 seconds.
2. Calibrated top loading balance accurate to 0.01 grams.
3. Ringstand and clamps.
4. Separatory funnel with Nalgene stopcock which is calibrated to a discharge flow rate of 20±1 ml/second.
5. Filter paper—Eaton-Dikeman #90–140, available from Eaton-Dikeman, Division of Know/Ton Brothers, Mt. Holly Springs, Pa. 17065-0238.
6. Test apparatus consisting of the following:
    (a) Electronic timer measuring to 0.01 seconds. Available through J.G. McGuffey & Company, Peachtree City, Ga.
    (b) Strike-through plate: A 25 mm thick acrylic square strike-through plate is shown in FIGS. 8–10. The dimensions given in this figure are in mm. The strike-through plate 80 has marginal areas 82 which are available for optional weighting strips 84. Wire electrodes 86 having a diameter of 1 mm are placed in square-cut grooves 88 and may be secured with quick setting epoxy resin. These electrodes 86 must be kept clean. The total weight of the plate must be 225±5 grams. Care must be taken that the electrodes 86 are positioned as specified. The strike-through plate is available through R & L Engineering, Albany, Ga.

7. Surface wetness apparatus consisting of a compression weight which has a total weight equivalent to 0.5 psi (4.4 lbs), with a 4 inch by 2 inch base.
8. Tensiometer, DuNouy, available through Central Scientific Company, Chicago, Ill. or equivalent.
9. A 6 inch steel ruler.
10. A liquid container with a minimum capacity of 200 ml.

The test also uses a 1.59% Saline Test Solution prepared from deionized water.

Test Procedure

Begin testing by calibrating the flow rate of the separatory funnel. Using the Fisher Model 21 Tensiomat, record the surface tension of the test solution. Weigh the product to be tested and record the weight to 0.01 g. This is the "pre-weigh". Weigh overflow paper, e.g., paper towel or filter paper, and record the weight. Place the product on the overflow paper. If overflow ultimately occurs, reweigh the overflow paper to determine the amount of test fluid not absorbed into the test product. Place the strike-through plate over the center of the product. Attach a 2" length of tubing to the tip of the funnel. Tubing should be 1" above the product. Center the separatory funnel over the plate. Assure that the apparatus is in the middle and center of the product and that the plate contacts the surface of the product being tested. The extending electrodes should run parallel with the products length.

Tare a liquid container on the top loading balance. Measure desired amount test fluid into the container. Apply 40 ml of test fluid to the products at a flow rate of 20 cc/second. Repeat test with unused products with 60 ml of test fluid and 80 ml of test fluid with a flow rate of 20 cc/second. Ensure that the stopcock on the calibrated separatory funnel is closed. Ensure the electrodes on the strike-through plate are connected to the timer. Switch on the timer and reset to zero. Add the test fluid to the calibrated separatory funnel. Open the stopcock and discharge the test fluid. The initial flow of liquid will complete the electrical circuit and start the timer. The timer will stop when the liquid is absorbed into the test product and fallen below the level of the electrodes. As soon as the separatory funnel has been emptied, start the stopwatch/timer and time for 15 sec. Record the penetration time from the electronic timer in seconds to 0.01 sec. Remove test apparatus and weigh the tested product. Record the weight. This is recorded as the product post-weight.

When 15 seconds have elapsed, center a set of two 4"×2" pre-weighed filter papers on the product. The two filter papers are stacked one on the other. Apply the compression weight on top of the filter paper and restart start stopwatch/timer. Allow sample to remain under the compression weight for two minutes. Remove weight and filter paper. Weigh the filter paper to the nearest 0.01 gram. Record weight. Repeat the steps of this paragraph until less than 1 g of liquid is recorded.

Calculations

Calculate the fluid absorbed by subtracting the product pre-weight from the product post-weight. Record the value for fluid absorbed. Calculate the fluid absorbency rate by dividing the fluid absorbed by the time. Record this value in grams/sec to 0.1 g/sec. Calculate the amount of overflow by subtracting the overflow dry weight from the overflow wet weight. This is recorded as overflow amount. Calculate the difference in weight between each set of wet and dry filter papers to the nearest 0.01 gram. Continue to calculate the differences for each set of filter papers used using the following formula:

$$\text{Wet Filter Paper }(g) - \text{Dry Filter Paper }(g) = \text{Wetness Extracted }(g) \quad \text{(II)}$$

Record the sum of the differences from Calculation (II) as the total amount of surface wetness. The results of these measurements and calculations result in the strike-through and surface wetness data recorded in the Examples.

EXAMPLES

The present invention will be further understood by reference to the following specific Examples which are illustrative of the composition, form and method of producing the multilayered absorbent structure of the present invention. It is to be understood that many variations of composition, form and method of producing the absorbent structure would be apparent to those skilled in the art. The following Examples, wherein parts and percentages are by weight unless otherwise indicated, are only illustrative.

EXAMPLE 1

Four nonwoven fabric layers were chosen to illustrate the present invention. Five samples of an absorbent structure of the present invention were set up the following pore size sequence, starting with the topsheet:

| | Experimental | |
|---|---|---|
| Layer No. | Description | Average Pore Size |
| 1 | Bicomponent Fabric A | 200 µm |
| 2 | Fabric B | 140 µm |
| 3 | Bicomponent Fabric C | 190 µm |
| 4 | Fabric B | 140 µm |

The characteristics of the fabric layers are as follows:

Bicomponent Fabric A: a soft, thermobonded, semiabsorbent material manufactured from 3 denier bicomponent fibers (BASF 1050) having a thickness of about 30 mils (0.030 in) and a basis weight of about 0.7 oz/yd$^2$.

Fabric B: a soft, card-and-bind, blend of 6 denier and 3 denier polyester, semiabsorbent material having a thickness of about 0.017 inches and a basis weight of about 0.65 oz/yd$^2$ (Fiber Tech 68798, available from Fiber Tech, Rogers, Ark.).

Bicomponent Fabric C: a soft, thermobonded, semiabsorbent material manufactured from 3 denier bicomponent fibers (BASF 1050) having a thickness of about 20 mils (0,020 in) and a basis weight of about 0.5 oz/yd$^2$.

Five samples of a control configuration were also assembled with the conventional single funnel approach:

| | Control | |
|---|---|---|
| Layer No. | Description | Average Pore Size |
| 1 | Bicomponent Fabric A | 200 µm |
| 2 | Bicomponent Fabric C | 190 µm |
| 3 | Fabric B | 140 µm |
| 4 | Fabric B | 140 µm |

Each of these samples was placed over filter board, which stimulates an absorbent core, and then was tested for strike-through (penetration) time and for rewet (surface wetness). The test method is described above. The dosage in these tests was 15 ml of saline solution. The rewet test was performed by placing pre-weighed 2"×4" cuts of Eaton-Dikeman #901–140 filter paper on top of the absorbent sample and then placing a 2"×4" weight on top of the filter paper. The weight represents an applied pressure of 0.5 psi. After 2 minutes, the filter paper was reweighed and the difference was reported as the rewet.

The results were as follows:

|  | Experimental | Control |
| --- | --- | --- |
| Strike-through time (sec.): | 2.98 | 3.32 |
| Std. Dev. (sec.): | 0.25 | 0.28 |
| Rewet (g): | 0.58 | 1.22 |
| Std. Dev. (g): | 0.21 | 0.32 |

The results show that with the absorbent structure of the present invention, the rewet is substantially reduced compared with the control. The difference is statistically significant with 95% confidence. Also, the strike-through time is reduced with the absorbent structure of the present invention versus the control. This difference too is statistically significant.

Thus, a novel arrangement of layer has been achieved such that both the strike-through time and the rewet are reduced, improving product performance.

EXAMPLE 2

A control absorbent structure having a negative pore size gradient in a pleated absorbent core as described in Swieringa, U.S. Pat. No. 4,874,457, was prepared having the layers with the porosity identified below:

| Control | | |
| --- | --- | --- |
| Layer No. | Description | Average Pore Size |
| 1 | Bicomponent Fabric A | 190 μm |
| 2 | Bicomponent Fabric A | 190 μm |
| 3 | Fabric B | 140 μm |
| 4 | Fabric D | 60 μm |

The characteristics of the fabric layers are as follows:

Bicomponent Fabric A: As in Example 1.

Fabric B: As in Example 1.

Fabric D: A homogeneous blend of Syn-Pulp (available from Temple Inland, Silsbe, Tex.) and Aquakeep J-550 (available from Sumitomo, Japan). The blend is cast onto tissue and thermobonded.

This product also contains a powdered polyacrylate superabsorbent the third layer adjacent the lower surface of the absorbent core, with the superabsorbent predominantly positioned near the base of the core.

Next, a pleated core structure was made, similar to the control, but using the absorbent structure of the present invention (Product A). The layers of the core were as follows:

| Product A | | |
| --- | --- | --- |
| Layer No. | Description | Average Pore Size |
| 1 | Fabric E, top | 190 μm |
| 2 | Fabric E, middle | 100 μm |
| 3 | Fabric E, bottom and Fabric F, top | 770 μm |
| 4 | Fabric F, bottom | 60 μm |

The characteristics of the fabric layers are as follows:

Fabric E: Fabric E has a bottom layer of a uniform blend of 0.1 oz/yd$^2$, 10 denier synthetic bicomponent fiber (BASF 1088) and 0.1 oz/yd$^2$, 15 denier synthetic PET fiber (duPont 374W), a second layer of a uniform blend of 0.4 oz/yd$^2$, 3 denier synthetic bicomponent fiber (BASF 1050) and 0.5 oz/yd$^2$ cellulosic pulp fibers (Rayonier Pulp E-Type), and an upper layer of about 0.4 oz/yd$^2$, 3 denier synthetic bicomponent fiber (BASF 1050). This is described above in the specification as "the second fabric web".

Fabric F: A bottom layer of a uniform blend of 0.4 to 0.6 oz/yd$^2$, 3 denier synthetic bicomponent fiber (BASF 1050) and 1 to 1.5 oz/yd$^2$ cellulosic pulp fibers Rayonier Pulp E-Type, and an upper layer of a uniform blend of 0.1 oz/yd$^2$, 10 denier synthetic bicomponent fiber (BASF 1088) and 0.1 oz/yd$^2$, 15 denier synthetic PET fiber (duPont 374W). This is described above in the specification as "the first fabric web" without the optional 0.15 oz/yd$^2$ layer.

The same type of superabsorbent that was used in the control product was incorporated into the third layer of the absorbent structure of Product A.

The control and Product A were tested for Strike-through and re-wet as described for Example 1. There were 5 products tested of each design using a dosage of 40 ml. The results were as follows:

|  | Control | Product A |
| --- | --- | --- |
| Strike-through time (sec.): | 3.58 | 2.44 |
| Std. Dev. (sec.): | 1.16 | 0.24 |
| Rewet (g): | 4.02 | 1.36 |
| Std. Dev. (sec.): | 1.95 | 0.46 |

The results show that with the absorbent structure of the present invention, the strike-through time and the rewet is substantially reduced compared to the Control. The difference is statistically significant with 95% confidence.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method for manufacturing an absorbent structure which provides a substantially dry liquid-accepting surface after application of a quantity of liquid to the surface, comprising the steps of:
   a) forming a first thermobonded web by:
      i) depositing a first mass of fibers comprising a thermoplastic material on a moving web to form an upper layer having a first average pore size;
      ii) depositing a second mass of fibers comprising a thermoplastic material on the upper layer to form a middle layer having a second average pore size, less than the first average pore size;

iii) depositing a third mass of fibers comprising a thermoplastic material on the middle layer to form a bottom layer having a third average pore size; and iv) thermally bonding the layers to form the first thermobonded web;

b) forming a second thermobonded web by:

i) depositing fourth mass of fibers comprising a thermoplastic material on a moving web to form an upper layer having a fourth average pore size;

ii) depositing a fifth mass of fibers comprising a thermoplastic material on the upper layer to form a middle layer having a fifth average pore size, less than the fourth average pore size;

iii) depositing a sixth mass of fibers comprising a thermoplastic material on the middle layer to form a bottom layer having a sixth average pore size, greater than the fifth average pore size and greater than the second average pore size; and iv) thermally bonding the layers to form the second thermobonded web; and c) combining the first and second thermobonded webs to form the absorbent structure wherein the upper layer of the first web and the lower layer of the second web are in facing relation.

2. The method of claim 1 further comprising the step of inverting the first thermobonded web prior to the step of combining the first and second thermobonded webs.

3. The method of claim 2 which further comprises the step of applying a superabsorbent powder material to the upper fibrous layer of the first thermobonded web.

4. The method of claim 1 further comprising the step of corrugating the absorbent structure.

5. The method of claim 1 wherein the step of combining the first and second thermoplastic webs comprises embossing the webs together.

* * * * *